(12) United States Patent
Konno et al.

(10) Patent No.: US 6,458,379 B1
(45) Date of Patent: Oct. 1, 2002

(54) SHEET FOR WHITENING COSMETICS AND METHOD FOR USING THE SAME

(75) Inventors: Masayuki Konno, Osaka (JP); Takashi Kawasaki, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/419,372

(22) Filed: Oct. 15, 1999

(51) Int. Cl.⁷ .............................. A61K 9/70; A61F 13/00
(52) U.S. Cl. .................... 424/443; 424/401; 424/78.03; 514/474; 514/944
(58) Field of Search ................................ 424/401, 443, 424/78.03; 514/474, 944

(56) References Cited

U.S. PATENT DOCUMENTS 6,063,398 A * 5/2000 Gueret ........................ 424/443

FOREIGN PATENT DOCUMENTS

GB 2 265 086 * 9/1993

* cited by examiner

*Primary Examiner*—Jose'G. Dees
*Assistant Examiner*—Michael A. Williamson
(74) *Attorney, Agent, or Firm*—Kilyk & Bowersox, P.L.L.C.

(57) ABSTRACT

A sheet for whitening cosmetics comprises a sheet-like substrate and an adhesive layer which comprises a wet pressure-sensitive adhesive composition formed on the substrate. The whitening component includes vitamin C or its derivatives such as magnesium L-ascorbyl-2-phosphate, vitamin E nicotinate, kojic acid, hydroquinone, ellagic acid, albumin, galenical extracts, and rice bran extracts. Kojic acid and magnesium L-ascorbyl-2-phosphate are preferred. By contacting the adhesive layer with water and/or a hydrophilic medium such as alcohols, e.g., methanol, ethanol, etc., the wet pressure-sensitive adhesive composition exhibits excellent stickiness and excellent applicability to skin as well as excellent whitening effect with alleviating or eliminating stains, freckles, non-transparency, etc. on the skin.

19 Claims, No Drawings

SHEET FOR WHITENING COSMETICS AND METHOD FOR USING THE SAME

FIELD OF THE INVENTION

The present invention relates to a sheet for whitening cosmetics and to a method for using the same. More particularly, it relates to a sheet for whitening cosmetics for alleviating or eliminating stains, freckles, non-transparency, etc. due to deposition of pigments or pigmentation on the surface of a skin and to a method for using such a sheet for whitening cosmetics.

DESCRIPTION OF THE RELATED ART

Cosmetics which exhibit various effects are commercially available. Among them, attention has been being increasingly paid to those cosmetics which exhibit an effect of causing a skin to look whiter, i.e., a so-called whitening effect. Stains, freckles, non-transparency, etc. once occurred on the skin, in particular, the skin of a face, are difficult to be eliminated. Many companies have developed preparations for preventing these symptoms and put them on the market.

It is generally believed that exposure of a skin to ultraviolet rays generates melanine pigment in the skin, which causes such a pigmentation. Therefore, whitening cosmetics which inhibit the generation of or remove the melanine pigments in the skin to prevent various symptoms attributable to the deposition of pigments have been developed and there have been various commercial products. Most of them are liquid or cream-like products.

However, cosmetics in the form of liquid or cream have the problems that the amount (dose) of the cosmetic applied to a skin surface is usually not constant, varying from site to site of application on the skin and it is difficult to efficiently apply the whitening component onto a skin surface and that the cosmetics are wiped off by contact with other things, e.g., hand, cloth, etc. Therefore, use of the cosmetics must be continued for a long time before they exhibit a satisfactory whitening effect.

Generally, cosmetics in the form of liquid or cream are applied with fingers and/or palms and therefore the cosmetics adhere to the fingers and/or palms of users. Therefore, it is often the case that their washing is necessary, which will be troublesome to most of the users.

SUMMARY OF THE INVENTION

That is, an object of the present invention is to provide a whitening cosmetic containing a whitening component of which it is easy to make the amount (dose) applied to a skin surface constant.

Another object of the present invention is to provide a whitening cosmetic which does not adhere to fingers and/or palms of a user when applied to a skin surface with the fingers and/or palms.

Still another object of the present invention is to provide a whitening cosmetic which can be stored with ease and readily applied in a wet state to a skin surface upon use.

Yet another object of the present invention is to provide a method for using such whitening cosmetics as described above.

Accordingly, the present inventors have made extensive research with view to obviating the above-described problems and as a result, they have now found that the above-described objects can be attained by the provision of a sheet-like whitening cosmetic comprising a substrate in the form of a sheet having formed on a surface thereof an adhesive layer comprising a wet pressure-sensitive adhesive composition, which readily exhibits stickiness upon contact with or exposure to water or the like, i.e., thus completing the present invention.

That is, in a first aspect, the present invention provides a sheet for whitening cosmetics, comprising a sheet-like substrate and an adhesive layer comprising a wet pressure-sensitive adhesive composition formed on the substrate.

Here, the wet pressure-sensitive adhesive composition may comprise a water-soluble base material and a wetting agent.

The water-soluble base material may comprise a water-soluble polymer.

The water-soluble polymer may be at least one compound selected from the group consisting of polyvinylpyrrolidone, polyvinyl alcohol, sodium alginate, sodium polyacrylate, potassium polyacrylate, polyacrylamide, carboxymethylcellulose, gum Arabic, and polymethyl vinyl ether.

The wetting agent may be a polyhydric alcohol.

The polyhydric alcohol may be at least one compound selected from the group consisting of glycerin, sorbitol, polyethylene glycol, propylene glycol, polypropylene glycol, 1,3-propanediol, 1,4-butanediol.

The polyhydric alcohol is preferably glycerin.

The sheet-like substrate preferably has a water vapor permeability.

The sheet-like substrate may comprise a fabric or a laminate sheet of a fabric and a water vapor permeable plastic film.

The sheet-like substrate may comprise a fabric or a laminate sheet of a fabric and a water vapor permeable plastic film.

The sheet for whitening cosmetics may further comprise a separator provided on a surface of the adhesive layer opposite to the sheet-like substrate.

The whitening component may be at least one substance selected from the group consisting of vitamin C or its derivatives, vitamin E nicotinate, kojic acid, hydroquinone, ellagic acid, albumin, galenical extracts, and rice bran extracts.

The whitening component is preferably kojic acid or rice bran extracts.

The whitening component is preferably magnesium L-ascorbyl-2-phosphate.

The wet pressure-sensitive adhesive composition may be in a dry state.

The wet pressure-sensitive adhesive composition may be in a wet state after it has once been dried.

In a second aspect, the present invention provides a method for using a sheet for whitening cosmetics as described above, comprising the steps of:

contacting the sheet for whitening cosmetics with water and/or a hydrophilic medium prior; and then applying the sheet to an application site on a surface of skin where application of the sheet is desired.

Here, the water and/or hydrophilic medium may be contacted with a surface of the adhesive layer of said whitening cosmetic sheet.

The water and/or hydrophilic medium may be contacted with the application site on a surface of skin where application of said sheet is desired.

The above and other objects, effects, features and advantages of the present invention will become more apparent from the following description of preferred embodiments.

DETAILED DESCRIPTION OF THE INVENTION

Here, the term "sheet for whitening cosmetics" is also referred to as "whitening cosmetic sheet."

The wet pressure-sensitive adhesive composition used in the present invention is a composition which forms a film when an adhesive layer formed in the form of a sheet is applied to an application site and left to stand for a predetermined time to dry it. The composition is not limited particularly so long as it exhibits stickiness upon contact with a hydrophilic medium usually used in cosmetics, such as water, methanol, ethanol, or mixtures of these, coated or otherwise applied upon use. More specifically, a composition comprising a water-soluble base material such as water-soluble polymer and a wetting agent blended therein is used advantageously.

The water-soluble base material which can be used preferably includes polyvinylpyrrolidone, polyvinyl alcohol, sodium alginate, sodium polyacrylate, potassium polyacrylate, polyacrylamide, carboxymethylcellulose, gum Arabic, polymethyl vinyl ether, etc. Particularly preferred are polyvinyl alcohol, polyvinylpyrrolidone, polyacrylic acid salts (Na salt, K salt, etc.). The molecular weight of water-soluble polymer used as a water-soluble base material is not limited particularly so long as the above-described properties of wet pressure-sensitive adhesive composition can be exhibited but usually, a molecular weight in the range of from 50,000 to 2,000,000 is preferred. If the molecular weight is below 50,000, the base material tends to remain on the skin surface while with a molecular weight of above 2,000,000, the viscosity of a solution of composition upon the production is too high so that it is frequently the case that production of the wet pressure-sensitive adhesive composition tends to be difficult.

The wetting agent which can be used in the present invention includes glycols such as glycerin, sorbitol, polyethylene glycol, propylene glycol, and polypropylene glycol, polyhydric alcohols such as diols, e.g., 1,3-propanediol and 1,4-butanediol. These can be used singly or two or more of them can be used in combination. Out of these, glycerin is particularly preferable since precedent examples of use thereof are amply available and thus its safety has been well known. The amount of wetting agent to be added is not limited particularly so long as the properties of the above-described wet pressure-sensitive adhesive composition can be exhibited and may be selected appropriately in combination with the water-soluble base material. Usually, the addition amount of wetting agent in the range of 40% by weight or less is preferred. If the addition amount of wetting agent is above 40% by weight, the film strength of the adhesive layer is decreased to frequently cause adhesive deposit or residue.

As described above, the wet pressure-sensitive adhesive composition has properties that it is brought in humid or wet condition when it is brought in contact with water or a hydrophilic medium upon use and forms a film upon drying after it is applied to a surface of skin such as a face skin. Therefore, in order to make it easy for water or hydrophilic medium in the wet pressure-sensitive adhesive composition to evaporate, various inorganic or organic fillers which are sparingly soluble or insoluble may be blended or various plasticizers may be blended in the above-described composition in order to impart flexibility to the adhesive layer.

Such an inorganic filler includes, for example, inorganic oxides or composite oxides such as silica, alumina, zeolite, zinc oxide, titanium oxide, talc, clay, kaolin, silicic anhydride, and glass powder, inorganic compounds such as barium sulfate, calcium carbonate, hydroxylapatite, ceramics, and carbon, metals such as simple metals or alloys composed of two or more metals, etc. The organic filler includes, for example, fiber forming polymer compounds such as cellulose, silk, polyester, and polyolefin, organic polymer compounds such as polyacrylic acid esters, polymethacrylic acid esters, and polystyrene. Out of these, preferred are silicic anhydride and zeolite.

The addition amount of filler may be set appropriately. Usually, it is preferred that the filler have a maximum diameter of about 150 $\mu$m, and an average particle diameter of usually 50 $\mu$m or less. A particle diameter larger than the above is not preferable since rough or sandy feeling tends to occur to a user when the adhesive layer is applied to the skin.

On the other hand, examples of the plasticizer include glycols such as ethylene glycol diethylene glycol, triethylene glycol, hexamethylene glycol, polyethylene glycol, propylene glycol, dipropylene glycol, polypropylene glycol, 1,3-butylene glycol, and 1,4-butylene glycol, sugar alcohols such as sorbitol, and mannitol, glycerides such as lanolin, lecithin, and olive oil, glycerin, diglycerin, polyglycerin, etc. Out of these, glycols and glycerin are preferred. The addition amount of plasticizer may be set appropriately.

Further, if needed, perfumes, antiseptic/mildew-proofing agents, colorants, etc. may be blended appropriately.

Furthermore, surfactants may be added in the wet pressure-sensitive adhesive composition in advance in the case where the activity of whitening component to penetrate into the skin when the gel sheet is applied is to be increased or where oil-soluble components are to be blended in the adhesive layer. As such a surfactant, there can be used one or more of cationic surfactants such as quaternary ammonium salts and alkylpyridinium salts, anionic surfactants such as sodium alkylbenzenesulfonate and sodium dodecylsulfonate, nonionic surfactants such as polyoxyethylene alkyl ether and fatty acid esters of sucrose, amphoteric surfactants such as N-alkyl-N,N-dimethylammonium betaine, etc.

In the present invention, the whitening component to be blended in the adhesive layer is not limited particularly so long as it exhibits a whitening effect by preventing the deposition of or removing the pigments in the skin. More particularly, there can be cited those substances which have an effect of inhibiting the generation of melanine which causes pigmentation, those substances which have an effect of improving the moisture retention of corneum of the skin, those substances which improves blood circulation in the skin in order to remove non-transparency, those substances which have an effect of removing corneum which contains melanine, etc. Specifically, vitamin C and its derivatives, e.g., magnesium L-ascorbyl-2-phosphate, vitamin E nicotinate, kojic acid, hydroquinone, ellagic acid, albumin, and galenical extracts (chamomile extracts, saxifrage (*Saxifraga stolonifera* Meerb.) extracts, scuttellaria root extracts, etc.) are preferred. It is effective to blend at least one out of them. Particularly preferred are kojic acid, vitamin C and its derivatives, e.g., magnesium L-ascorbyl-2-phosphate.

The content of the whitening component described above is not limited particularly so long as it exhibits whitening effect. Usually, addition of it in the adhesive layer in an amount on the order of about 0.005 to about 10% by weight, preferably 0.01 to 5% by weight, more preferably 0.1 to 3% by weight, can give a sufficient whitening effect.

The whitening component may be added in the form of a substance itself or in the form of a whitening cosmetic such as beauty wash or cream containing a whitening component. In particular, liquid preparations are advantageous since they are highly compatible with the wet pressure-sensitive adhesive composition and can be homogeneously mixed therewith without difficulty during its production.

The whitening component can be mixed with water and/or a hydrophilic medium such as an alcohol homogeneously to prepare a composition for an adhesive layer (liquid), which is coated on a surface of a separator or on a sheet-like substrate and subsequently dried to form an adhesive layer. Note that when the adhesive layer is formed by drying, it is unnecessary to completely remove the water or hydrophilic medium but from several percents by weight to several tens percents by weight of them may remain in the coated film. However, taking into consideration adhesiveness and storage stability, the content of water and/or hydrophilic medium is preferably 40% by weight or less, more preferably 30% by weight ore less, based on the weight of the wet pressure-sensitive adhesive composition.

The adhesive layer thus formed is adjusted to have a thickness of usually 20 to 500 $\mu$m, preferably 30 to 300 $\mu$m. If it is below 20 $\mu$m, the thickness tends to be too small to sufficiently contain the whitening component therein while if the thickness is above 500 $\mu$m, the flexibility of the adhesive layer is poor so that when the sheet is applied to a curved surface of a skin, users tend to feel strange or unfitted.

The sheet-like substrate which can be used in the present invention is not limited particularly so long as it is in the form of a sheet. However, it is preferred to use a substrate having a water vapor permeability, for example, cloth such as woven fabric, unwoven fabric, or knitted fabric or paper, porous film or other water vapor permeable plastic film. The material of the substrate may be synthetic or natural organic polymers such as nylon, polyester, polypropylene, polyurethane, cellulose, and polytetrafluoroethylene. These may be used singly or two or more may be used in combination. Among these, a laminate sheet made of a combination of cloth such as unwoven fabric and a plastic film having a water vapor permeability is preferable because such is excellent in air permeability (moisture evaporation) and in a reduction in production costs.

It is preferred that a separator be laminated on a surface of the adhesive layer on which surface it is to be applied to a skin (a surface opposite to the substrate) so that the adhesive layer can be kept hygienic or sheets for whitening cosmetics can be stored by placing one upon another or in the form of a roll. As such a separator, polyester film, polyethylene film, polypropylene film, release-treated paper, etc. may be used. The separator has a thickness on the order of usually about 25 to about 300 $\mu$m, preferably 38 to 200 $\mu$m. If the thickness of the separator is below 25 $\mu$m, the separator is difficult to produce or handle while with a thickness above 300 $\mu$m, the separator is too bulky to be stored conveniently.

The sheet for whitening cosmetics of the present invention is applied in the following manner. That is, prior to its application, the surface of the adhesive layer and/or a target site where the sheet of the present invention is to be applied is made wet by contacting water and/or a hydrophilic medium, for example, by coating or spraying the water and/or hydrophilic medium. That is, water or a hydrophilic medium is contacted directly onto the surface of the adhesive layer of the sheet or the water and/or hydrophilic medium coated or sprayed onto the application site is transferred to the surface of the adhesive layer of the sheet upon application of the sheet to the application site, i.e., the water and/or hydrophilic medium is contacted indirectly onto the surface of the adhesive layer. In each case, upon contact with the water and/or hydrophilic medium, the wet pressure-sensitive adhesive composition in the adhesive layer is dissolved or swells to exhibit stickiness. As a result, the sheet for whitening cosmetics of the present invention can be applied to a skin surface such as a face skin such that it can stick to the skin surface closely tracing the unevenness thereon, so that the whitening component contained in the application of the sheet can act on the skin surface effectively. After the application of the sheet to the skin surface, the water and/or hydrophilic medium in the adhesive layer of the sheet are/is evaporated from the side surface of the adhesive layer or through the back surface of the substrate and the inner cohesive power of the adhesive layer is gradually recovered according as the evaporation proceeds and the wet pressure-sensitive adhesive composition in the adhesive layer once in a wet state forms a film on the skin surface while it is kept adhered closely to the skin surface. Therefore, the cosmetic sheet of the present invention can retain close adhesion to the skin so that the whitening component is not wiped off unlike the conventional whitening cosmetics and hence the cosmetic sheet of the present invention can exhibit its whitening effect very efficiently and uniformly all over the site of skin surface where it is applied.

When the sheet for whitening cosmetics of the present invention is to be peeled off from the skin, it may be peeled off as it is. In case where the adhesion to the skin is strong and there is the fear that pain is felt by a user upon peeling it off, water and/or a hydrophilic medium may be provided on the back surface of the substrate by coating or spraying so that the water and/or hydrophilic medium can be transferred to the adhesive layer to thereby decrease the inner cohesive force of the adhesive layer. This helps peeling off of the sheet without pain and without difficulty.

EXAMPLES

Hereafter, the present invention will be described in detail by examples. However, the present invention should not construed as being limited thereto.

Example 1

To a mixture of 50% by weight of polyvinylpyrrolidone having a weight average molecular weight of 1,200,000, 15% by weight of glycerin, and 35% by weight of silicic anhydride was added a suitable amount of water and then kojic acid in an amount such that its concentration in a dried adhesive layer is 2% by weight to obtain a liquid preparation of wet pressure-sensitive adhesive composition.

This liquid preparation was uniformly coated on a release-treated surface of a 50 $\mu$m thick separator (polyester film) and polyester unwoven fabric (basis weight 40 g/m$^2$) was laminated thereon, followed by drying to fabricate a whitening cosmetic sheet of the invention. The fabricated whitening cosmetic sheet had a 150 $\mu$m thick adhesive layer whose water content was 22% by weight.

Example 2

To a mixture of 70% by weight of sodium polyacrylate having a weight average molecular weight of 100,000 and 30% by weight of glycerin was added a suitable amount of water and then kojic acid in an amount such that its concentration in a dried adhesive layer is 1% by weight to obtain a liquid preparation of wet pressure-sensitive adhesive composition.

Then, the liquid preparation was coated uniformly on a laminate film made of a perforated polyester film (12 μm thick)/rayon unwoven fabric (basis weight: 30 g/m²), more particularly on the rayon unwoven fabric side thereof, followed by drying to fabricate a whitening cosmetic sheet of the present invention. The fabricated whitening cosmetic sheet had a 150 μm thick adhesive layer whose water content was approximately 0% by weight.

Example 3

Whitening cosmetic sheets were fabricated in the same manner as in Example 1 except that instead of kojic acid, magnesium L-ascorbyl-2-phosphate was blended in concentrations of 2% by weight and 0% by weight, respectively, in a dried adhesive layer. The fabricated whitening cosmetic sheets each had a 200 μm thick adhesive layer whose water content was 22% by weight.

Example 4

A whitening cosmetic sheets was fabricated in the same manner as in Example 1 except that instead of kojic acid, rice bran extracts were blended in a concentration of 1% by weight in a dry adhesive layer. The fabricated whitening cosmetic sheet had a 200 μm thick adhesive layer whose water content was 15% by weight.

Comparative Example 1

A whitening cosmetic sheet was fabricated in the same manner as in Example 1 except that no kojic acid was blended.

Comparative Example 2

A whitening cosmetic sheet was fabricated in the same manner as in Example 3 except that no magnesium L-ascorbyl-2-phosphate was blended.

Application tests of the whitening cosmetic sheets of Examples and Comparative Examples thus fabricated were performed by the following test method and evaluation method. Table 1 shows the results of evaluation of each sheet. [Application Test]

The whitening cosmetic sheets fabricated in Examples 1 to 4 and Comparative Examples 1 and 2 were each cut to a shape of ellipse with a size of 30 mm (minor axis)×50 mm (major axis). After washing the face of a volunteer, the water on the face was not wiped off and in this state each cosmetic sheet was applied to the face. The application test was conducted on 18 female volunteers who had stains, freckles, non-transparency or the like on the cheek and have an experience of having used a whitening cosmetic previously. The applicability, adhesive residue after peeling off, whitening efficacy, and skin irritation were evaluated based on the following criteria.

<Applicability>

After the application of the cosmetic sheet to the skin, the condition of adhesion of the cosmetic sheet to the skin was observed. Evaluation was made by the following rating:

| Good: | The sheet adhered to the skin sufficiently after 12 hours |
| Poor: | The sheet peeled off before 12 hour had elapsed. |

<Adhesive Residue>

After the cosmetic sheet was applied to the skin for 12 hour, the sheet was peeled off and the occurrence of adhesive residue was checked. Evaluation was made on the following rating:

| Good: | No adhesive residue was observed. |
| Poor: | Adhesive residue was observed. |

<Efficacy>

Eighteen (18) female volunteers repeated 8 hours' application of the cosmetic sheet daily for 3 month and whether or not the whitening effect was obtained was judged.

Evaluation was made based on following rating:

| Good: | 70 to 100% of the volunteers answered that the whitening effect was obtained. |
| Fairly good: | 40 to 69% of the volunteers answered that the whitening effect was obtained. |
| Poor: | 0 to 39% of the volunteers answered that the whitening effect was obtained. |

<Skin Irritation>

After the cosmetic sheet was applied to the skin for 12 hour, the sheet was peeled off and pain or other irritation was evaluated. Evaluation was made on the following rating:

| Good: | No irritation was felt. |
| Poor: | Upon peeling redness or the other irritation was observed on the skin. |

The results of evaluation are shown in Table 1.

TABLE 1

| | Applicability | Adhesive residue | Efficacy | Skin irritation |
|---|---|---|---|---|
| Example 1 | Good | Good | Good | Good |
| Example 2 | Good | Good | Good | Good |
| Example 3 | Good | Good | Good | Good |
| Example 4 | Good | Good | Fairly good | Good |
| Comparative Example 1 | Good | Good | Poor | Good |
| Comparative Example 1 | Good | Good | Poor | Good |

<Storage Stability>

After storing the whitening cosmetic sheets fabricated in Examples 1 and 3 at room temperature (20° C.) at a relative humidity of 40% for 6 hours, application tests were conducted similarly. The whitening cosmetic sheets of Examples 1 and 3 were good in both efficacy and skin irritation. In this case, the whitening cosmetic sheet of Example 3 (water content: approximately 0% by weight) was slightly better in storage stability than that of Example 1.

As described above, the whitening cosmetic sheet of the present invention has an adhesive layer comprising a wet pressure-sensitive adhesive composition containing a whitening component, formed on a substrate in the form of a sheet and the wet pressure-sensitive adhesive composition exhibits excellent stickiness or adhesion upon contact with water or a hydrophilic medium coated on the adhesive layer or skin, and the adhesive layer closely adheres to the skin surface for a long period of time so that stains, freckles, non-transparency, etc. can be eliminated efficiently by a simple and easy manner.

Moreover, since the water or hydrophilic medium contained in the adhesive layer evaporates through the body of substrate during application, there occurs no phenomenon of adhesive deposit or residue upon peeling and the peeling operation is easy.

Furthermore, the whitening cosmetic of the present invention is molded into a sheet unlike the conventional liquid or cream-like whitening cosmetics and users do not have to take care for removing the cosmetic which adhered on their fingers or palm upon application of the cosmetic so that it can be handled very easily. In addition, the whitening component contained in the adhesive layer is protected from contacting other things by a sheet-shaped substrate, so that it cannot be wiped off during its application and it can exhibit a whitening effect efficiently.

The present invention has been described in detail with respect to an embodiment, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. A sheet for whitening cosmetics, comprising a sheet substrate and an adhesive layer, and a separator layer having a thickness of about 25 to about 300 $\mu$m, laminated on the surface of said adhesive layer opposite said sheet substrate, said adhesive layer comprising a wet pressure-sensitive adhesive composition and a whitening component formed on said substrate, wherein said wet pressure-sensitive adhesive composition comprises a water soluble base material having a molecular weight in the range of from 50,000 to 2,000,000, and a wetting agent or polyhydric alcohol in the range of 40% by weight or less based on the wet pressure-sensitive adhesive composition, said wet pressure-sensitive adhesive composition containing a filler having an average particle diameter of 50 $\mu$m or less, and said adhesive layer having a thickness of 20 to 500 $\mu$m.

2. The sheet for whitening cosmetics as claimed in claim 1, wherein the wet pressure-sensitive adhesive composition comprises a water-soluble base material and a wetting agent.

3. The sheet for whitening cosmetics as claimed in claim 2, wherein the water-soluble base material comprises a water-soluble polymer.

4. The sheet for whitening cosmetics as claimed in claim 3, wherein the water-soluble polymer is at least one compound selected from the group consisting of polyvinylpyrrolidone, polyvinyl alcohol, sodium alginate, sodium polyacrylate, potassium polyacrylate, polyacrylamide, carboxymethylcellulose, gum Arabic, and polymethyl vinyl ether.

5. The sheet for whitening cosmetics as claimed in claim 1, wherein the wetting agent is a polyhydric alcohol.

6. The sheet for whitening cosmetics as claimed in claim 5, wherein the polyhydric alcohol is at least one compound selected from the group consisting of glycerin, sorbitol, polyethylene glycol, propylene glycol, polypropylene glycol, 1,3-propanediol, 1,4-butanediol.

7. The sheet for whitening cosmetics as claimed in claim 6, wherein the polyhydric alcohol is glycerin.

8. The sheet for whitening cosmetics as claimed in claim 1, wherein said sheet substrate has a water vapor permeability.

9. The sheet for whitening cosmetics as claimed in claim 1, wherein said sheet substrate comprises a fabric or a laminate sheet of a fabric and a water vapor permeable plastic film.

10. The sheet for whitening cosmetics as claimed in claim 8, wherein said sheet substrate comprises a fabric or a laminate sheet of a fabric and a water vapor permeable plastic film.

11. The sheet for whitening cosmetics as claimed in claim 1, further comprising a separator provided on a surface of said adhesive layer opposite to said sheet substrate.

12. The sheet for whitening cosmetics as claimed in claim 1, wherein the whitening component is at least one substance selected from the group consisting of vitamin C or its derivatives, vitamin E nicotinate, kojic acid, hydroquinone, ellagic acid, albumin, galenical extracts, and rice bran extracts.

13. The sheet for whitening cosmetics as claimed in claim 12, wherein the whitening component is kojic acid or rice bran extracts.

14. The sheet for whitening cosmetics as claimed in claim 12, wherein the whitening component is magnesium L-ascorbyl-2-phosphate.

15. The sheet for whitening cosmetics as claimed in claim 1, wherein the wet pressure-sensitive adhesive composition is in a dry state.

16. The sheet for whitening cosmetics as claimed in claim 1, wherein the wet pressure-sensitive adhesive composition is reconditioned into a wet state.

17. A method for using a sheet for whitening cosmetics as claimed in claim 1, comprising the steps of:

contacting said sheet for whitening cosmetics with water and/or a hydrophilic medium; and then applying said sheet to an application site on a surface of skin where application of said sheet is desired.

18. The method as claimed in claim 17, wherein the water and/or hydrophilic medium are/is contacted with a surface of the adhesive layer of said whitening cosmetic sheet.

19. The method as claimed in claim 17, wherein the water and/or hydrophilic medium are/is contacted with the application site on a surface of skin where application of said sheet is desired.

* * * * *